(12) United States Patent
Cohen et al.

(10) Patent No.: US 10,940,147 B2
(45) Date of Patent: *Mar. 9, 2021

(54) EARLY TREATMENT OF CMT DISEASE

(71) Applicant: Pharnext, Issy les Moulineaux (FR)

(72) Inventors: Daniel Cohen, Saint Cloud (FR); Ilya Chumakov, Vaux le Pénil (FR); Rodolphe Hajj, St. Germain en Laye (FR); Aude Milet, Antony (FR); Serguei Nabirochkin, Chatenay Malabry (FR); Klaus-Armin Nave, Göttingen (DE); Thomas Prukop, Duderstadt (DE); Michael Sereda, Göttingen (DE)

(73) Assignee: Pharnext, Issy-les-Moulineaux (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/505,000

(22) Filed: Jul. 8, 2019

(65) Prior Publication Data

US 2020/0030314 A1 Jan. 30, 2020

Related U.S. Application Data

(63) Continuation of application No. 15/619,074, filed on Jun. 9, 2017, now Pat. No. 10,383,870.

(60) Provisional application No. 62/348,276, filed on Jun. 10, 2016.

(51) Int. Cl.
| | | |
|---|---|---|
| *A61K 31/485* | (2006.01) | |
| *A61K 31/197* | (2006.01) | |
| *C12Q 1/6883* | (2018.01) | |
| *A61K 31/047* | (2006.01) | |

(52) U.S. Cl.
CPC .......... *A61K 31/485* (2013.01); *A61K 31/047* (2013.01); *A61K 31/197* (2013.01); *C12Q 1/6883* (2013.01); *C12Q 2600/156* (2013.01)

(58) Field of Classification Search
CPC .............. A61K 2300/00; A61K 31/047; A61K 31/197; A61K 31/485; C12Q 1/6883; C12Q 2600/156

See application file for complete search history.

(56) References Cited

U.S. PATENT DOCUMENTS

| | | | |
|---|---|---|---|
| 7,592,372 B2 | 9/2009 | Osugi | |
| 8,716,269 B2 | 5/2014 | Cohen et al. | |
| 8,992,891 B2 | 3/2015 | Cohen et al. | |
| 9,393,241 B2 | 7/2016 | Cohen et al. | |
| 9,427,436 B1 | 8/2016 | Cohen et al. | |
| 9,566,275 B2 | 2/2017 | Cohen et al. | |
| 10,322,101 B2 | 6/2019 | Cohen et al. | |
| 2003/0069213 A1 | 4/2003 | Il et al. | |
| 2005/0038062 A1 | 2/2005 | Burns et al. | |
| 2005/0187290 A1 | 8/2005 | Fontes et al. | |
| 2005/0220863 A1 | 10/2005 | Han | |
| 2007/0099947 A1 | 5/2007 | Dean et al. | |
| 2007/0110801 A1 | 5/2007 | Perovitch et al. | |
| 2007/0299098 A1 | 12/2007 | Tanabe | |
| 2008/0206332 A1 | 8/2008 | Kidney et al. | |
| 2008/0255062 A1 | 10/2008 | Fernyhough et al. | |
| 2012/0040940 A1 | 2/2012 | Cohen et al. | |
| 2012/0088744 A1 | 4/2012 | Cohen et al. | |
| 2012/0270836 A1 | 10/2012 | Cohen et al. | |
| 2013/0059676 A1 | 3/2013 | Angeli | |
| 2013/0085122 A1 | 4/2013 | Cohen et al. | |
| 2013/0090307 A1 | 4/2013 | Cohen et al. | |
| 2014/0178463 A1 | 6/2014 | Cohen et al. | |
| 2015/0157626 A1 | 6/2015 | Cohen et al. | |
| 2016/0113867 A1 | 4/2016 | Cohen et al. | |
| 2017/0165256 A1 | 6/2017 | Cohen et al. | |
| 2018/0250290 A1 | 9/2018 | Cohen et al. | |

FOREIGN PATENT DOCUMENTS

| | | |
|---|---|---|
| CA | 2727064 A1 | 12/2009 |
| DE | 102006016990 A1 | 10/2007 |
| EP | 0778023 A1 | 6/1997 |
| EP | 2065038 A1 | 6/2009 |
| EP | 2263665 A1 | 12/2010 |
| WO | 2000020024 A2 | 4/2000 |
| WO | 0249607 A2 | 6/2002 |
| WO | 2003077867 A2 | 9/2003 |
| WO | 2004006911 A2 | 1/2004 |
| WO | 2004019938 A1 | 3/2004 |
| WO | 2004103263 A2 | 12/2004 |
| WO | 2005032555 A2 | 4/2005 |
| WO | 2005053612 A2 | 6/2005 |
| WO | 2006117573 A1 | 11/2006 |
| WO | 2007134077 A2 | 11/2007 |
| WO | 2007134136 A2 | 11/2007 |
| WO | 2009068668 A1 | 6/2009 |

(Continued)

OTHER PUBLICATIONS

Fledrich et al., "Soluble neuregulin-1 modulates disease pathogenesis in rodent models of Charcot-Marie-Tooth disease 1A," Nature Medicine, vol. 20, 2014, pp. 1055-1061.

Gabreëls-Festen et al., "Charcot-Marie-Tooth disease type 1A: morphological phenotype of the 17p duplication versus PMP22 point mutations," Acta Neuropathologica, vol. 90, 1995, pp. 645-649.

Chumakov et al., "Polytherapy with a combination of three repurposed drugs (PXT3003) down-regulates Pmp22 over-expression and improves myelination, axonal and functional parameters in models of CMT1A neuropathy," Orphanet Journal of Rare Diseases, vol. 9, 2014, p. 201.

(Continued)

*Primary Examiner* — Umamaheswari Ramachandran
(74) *Attorney, Agent, or Firm* — Andrea L. C. Reid; Joseph W. Arico; Dechert LLP

(57) ABSTRACT

The present invention provides methods for treating, preventing, or delaying the onset of Charcot-Marie-Tooth Disease type 1A (CMT1A), by administering to a subject in need thereof a combination comprising baclofen, sorbitol and naltrexone, or a pharmaceutically acceptable salt thereof.

18 Claims, 8 Drawing Sheets

Specification includes a Sequence Listing.

(56) References Cited

FOREIGN PATENT DOCUMENTS

| WO | 2009153291 A1 | 12/2009 |
| WO | 2010139627 A1 | 12/2010 |
| WO | 2011054759 A1 | 5/2011 |
| WO | 2012117076 A2 | 9/2012 |
| WO | 2014195394 A1 | 12/2014 |

OTHER PUBLICATIONS

Shy et al., "Reliability and validity of the CMT neuropathy score as a measure of disability," Neurology, vol. 64, 2005, pp. 1209-1214.
Murphy et al., "Reliability of the CMT neuropathy score (second version) in Charcot-Marie-Tooth disease," Journal of the Peripheral Nervous System, vol. 16, 2011, pp. 191-198.
Burns et al., "Validation of the Charcot-Marie-Tooth disease pediatric scale as an outcome measure of disability," Annals of Neurology, vol. 71, 2012, pp. 642-652.
Graham et al., "A modified peripheral neuropathy scale: the Overall Neuropathy Limitations Scale," Journal of Neurology, Neurosurgery and Psychiatry, vol. 77, 2006, pp. 973-976.
Mandel et al., "A meta-analysis of randomized double-blind clinical trials in CMT1A to assess the change from baseline in CMTNS and ONLS scales after one year of treatment," Orphanet Journal of Rare Diseases, vol. 10, 2015, p. 74.
Sereda et al., "A transgenic rat model of Charcot-Marie-Tooth disease," Neuron, vol. 16, 1996, pp. 1049-1060.
Meyer Zu Horste et al., "Antiprogesterone Therapy Uncouples Axonal Loss from Demyelination in a Transgenic Rat Model of CMT1A Neuropathy," Annals of Neurology, vol. 61, 2007, pp. 61-72.
Rivlin et al., "Objective clinical assessment of motor function after experimental spinal cord injury in the rat," Journal of Neurosurgery, vol. 47, 1977, pp. 577-581.
Maxwell et al., "Two rapid and simple methods used for the removal of resins from 1.0 micron thick epoxy sections," Journal of Microscopy, vol. 112, 1978, pp. 253-255.
Prukop et al., "An Experimental Trial of an Early Onset Treatment with a Combinational Drug (PXT3003) Consisting of Baclofen, Naltrexone, Sorbitol in the CMT1A Rat Model," Peripheral Nerve Society Meeting, Presentation, Jun. 29, 2015 (19 pages).
No Author Listed, Peripheral Nerve Society Meeting Program, Jun. 27-Jul. 2, 2015 (238 pages).
Berenbaum et al., "Synergy, Additivism and Antagonism in Immunosuppression: A Critical Review," Clinical & Experimental Immunology, vol. 28, No Month Listed 1977, pp. 1-18.
International Search Report and Written Opinion issued by the European Patent Office as International Searching Authority for International Application No. PCT/EP2008/066468 dated Mar. 3, 2009 (14 pages).
International Search Report and Written Opinion issued by the European Patent Office as International Searching Authority for International Application No. PCT/EP2014/061664 dated Jun. 30, 2014 (10 pages).
Li et al., "Effect of Baclofen Combined with Neural Facilitation Technique on the Reduction of Muscular Spasm in Patients with Spinal Cord Injury," Neural Regeneration Research, vol. 2, No. 8, Aug. 2007, pp. 510-512.
Mhra, "Baclofen 5MG/5ML Oral Solution," Retrieved from the Internet <http://www.mhra.gov.uk/home/groups/par/documents/websiteresources/con094157.pdf> Aug. 2, 2010 (22 pages).
Pharminfotech, "Baclofen," Formulation in Pharmacy Practice—eMixt, Retrieved from the Internet <http://www.pharminfotech.co.nz/manual/Formulation/mixtures/baclofen.html> Aug. 31, 2011 (2 pages).
Weimer et al., "Medication-Induced Exacerbation of Neuropathy in Charcot-Marie-Tooth Disease," Journal of Neurological Science, vol. 242, No. 1-2, No Month Listed 2006, pp. 47-54.
Slavik, J. et al. "In Vitro Correlates of in Vivo Rapamycin Therapy in Patients with Multiple Sclerosis," Clinical Immunology, vol. 119, Jan. 1, 2006, p. S113.

Pomara, N. et al. "Mifepristone (RU 486) for Alzheimer's disease," Neurology, vol. 58, No. 9., May 1, 2002, p. 1436.
Gallagher, P. et al. "Persistent effects of mifepristone (RU-486) on cortisol levels in bipolar disorder and schizophrenia," Journal of Psychiatric Research, vol. 42, No. 12, Oct. 1, 2008, pp. 1037-1041.
Herrmann, D. N. et al. "Experimental Therapeutics in Hereditary Neuropathies: The Past, the Present and the Future," Neurotherapeutics, vol. 5, No. 4, Jan. 1, 2008, pp. 507-515.
Gironi, M. et al. "A pilot trial of low-dose naltrexone in primary progressive multiple sclerosis," Multiple Sclerosis, vol. 14, No. 8, Sep. 1, 2008, pp. 1076-1083.
Cintas, P. et al. "Drug therapy for symptomatic relief in ALS-Quels sont les traitements medicamenteux syptomatiques?" Revue Neurologique, vol. 162, Jun. 1, 2006, pp. 4S235-4S243.
Norris, F. H. et al. "Trial of Baclofen in Amyotrophic Lateral Sclerosis," Archives of Neurology, vol. 36, Nov. 1, 1979, pp. 715-716.
Lees, A. J. et al. "Baclofen in Parkinson's disease," Journal of Neurology, Neurosurgery & Psychiatry, vol. 41, Jan. 1, 1978, pp. 707-708.
Chemidex Pharma Ltd. "Lyflex 5mg/5ml Oral Solution" XP-002476376, retrieved from the Internet:http://emc.medicines.orq.uk/emc/assets/c/html/DisclavDoc.asp?documentID=14939, Apr. 14, 2008.
Wilcock, G. K. et al. "A placebo-controlled, double-blind trial of the selective AB-42 lowering agent, flurizan (MPC-7869, (R)-flurbiprofen) in patients with mild to moderate Alzheimer's disease," Alzheimer's & Dementia: The Journal of the Alzheimer's Association, vol. 1, No. 1, Jul. 1, 2005, p. S95, Abstract Feb. 1, 2005.
Written Opinion in International Application No. PCT/EP2010/057438, dated Nov. 4, 2010, pp. 1-19.
Bassi et al., "Encephalomyelitis with Thyrotoxicosis," Journal of Neurology, vol. 218, No Month Listed 1978, pp. 293-295.
Coffey et al., "Familial Trigeminal Neuralgia and Charcot-Marie-Tooth Neuropathy—Report of Two Families and Review," Surgical Neurology, vol. 35, Jan. 1, 1991, pp. 49-53.
Colombo et al., "Effects of the Combination of Naltrexone and Baclofen on Acquisition of Alcohol Drinking Behavior in Alcohol-Preferring Rats," Drug and Alcohol Dependence, vol. 77, No. 1, No Month Listed 2005, pp. 87-91.
Genetics Home Reference: Your Guide to Understanding Genetics Conditions. "Charcot-Mane-Tooth Disease," Dec. 11, 2012 <http://ghr.nlm.nih.gov/condition/charcot-marie-tooth-disease/show/print> (15 pages).
Grandis et al., "Current Therapy for Charcot-Marie-Tooth Disease," Current Treatment Options in Neurology, vol. 7, No. 1, No Month Listed 2005, pp. 23-31.
Magnaghi et al., "GABA Receptor-Mediated Effects in the Peripheral Nervous System—A Cross-Interaction with Neuroactive Steroids," Journal of Molecular Neuroscience, vol. 28, No. 1, No Month Listed 2006, pp. 89-102.
RightDiagnosis.com http://www.rightdiagnosis.com/n/neuropathy/subtypes.htm. Accessed Feb. 28, 2014 (pp. 1-9).
Stella et al., "Prodrug Strategies to Overcome Poor Water Solubility," Advanced Drug Delivery Reviews 59, No Month Listed 2007, pp. 677-694.
Zu Horste, G. M. et al. "Myelin disorders: Causes and Perspectives of Charcot-Marie-Tooth Neuropathy," Journal of Molecular Neuroscience, vol. 28, No. 1, Jan. 1, 2006, pp. 77-88.
Keltner, J. L. "Myotonic Pupils in Charcot-Marie-Tooth Disease, Successful Relief of Symptoms with 0.025% Pilocarpine," Achieves of Ophthalmology, vol. 93, No. 11, Jan. 1, 1975, pp. 1141-1148.
Chambliss, W.G., Sodium Acetate monograph in Handbook of Pharmaceutical Excipients 5th ed. (2006), pp. 654-655.
Jones, D., Chapter 1: Pharmaceutical Solutions for Oral Administration. In Pharmaceutics—Dosage Form and Design, 1E (2008).
SciFinder® Sorbitol Search Results (2018). Copyright © 2018 American Chemical Society (ACS).
Garcia et al., "Charcot-Marie-Tooth disease type 1A with 17p duplication in infancy and early childhood", Neurology, 50(4): 1061-1067 (1998).
CMTPEDS (http://calculator.cmtpeds.ord/,2015) (Year: 2018).

(56) References Cited

OTHER PUBLICATIONS

Haberlova et al., "Utility of Charcot-Marie-Tooth Neuropathy Score in children with type 1A disease", Pediatr Neurol., 43(6): 407-10 (2010).
Bird (NCBI, GeneReviews, 1998, p. 1-41).
CMT-NINDS, 2017 (https://www.ninds.nih.gov/Disorders/Patient-caregiver-education/Fact-sheets/Charcot-Marie-Tooth-Disease-Fact-Sheet, 2017).

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacaaacccc agacagttg                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagaaagcc agggaactc                                                  19
```

EARLY TREATMENT OF CMT DISEASE

CROSS REFERENCE TO RELATED APPLICATIONS

This application claims the benefit under 35 U.S.C. § 119(e) of U.S. Provisional Application No. 62/348,276, filed Jun. 10, 2016, the contents of which are incorporated herein in its entirety by reference.

FIELD OF THE INVENTION

The present invention relates to a new method of treatment of Charcot-Marie-Tooth disease. More particularly the invention relates to the administration, early in the pathological process of the disease, of a mix of baclofen, sorbitol, and naltrexone, or a pharmaceutically acceptable salt thereof, to a subject, for example a subject genetically predisposed to develop Charcot-Marie-Tooth type 1A.

SEQUENCE LISTING

The instant application contains a Sequence Listing which has been submitted electronically in ASCII format and is hereby incorporated by reference in its entirety. Said ASCII copy, created on Jun. 8, 2017, is named 389993-004US (154192)_SL.txt and is 685 bytes in size.

BACKGROUND OF THE INVENTION

Charcot Marie Tooth disease (CMT) is a rare, inherited and progressive peripheral neuropathy for which no etiological treatment is currently approved. CMT is highly heterogeneous both clinically and genetically. Charcot-Marie-Tooth type 1A (CMT1A) type is autosomal dominant and the most common type of CMT; it is caused, in the vast majority of cases, by a duplication of a fragment of chromosome 17p.11 that includes PMP22. The resulting overexpression of PMP22 is thought to be the main etiological cause of the dysmyelination, of the dysfunction and loss of peripheral nerves and of the muscle wasting that worsen in the course of the disease. Mutations of PMP22 gene, such as modification, deletion or splice mutation, have also been associated with CMT1A. Importantly, dysmyelination of peripheral nerve axons occurs early in postnatal development as was shown in PMP22 transgenic rats [1] and in CMT1A children aged 3.5 years [2]. PXT3003, a combination of (R/S) baclofen, sorbitol and naltrexone has been recently investigated in a one year, randomized, double-blind, placebo controlled phase 2 clinical trial. This trial showed evidence for an improvement beyond stabilization in an adult population of an average age above 40 [3].

Symptoms of CMT1A usually first appear in infancy, generally during the first two decades. Most frequently in the first 10 years, they include clumsiness of gait and deformity of feet. Difficulty in heel walking and areflexia or hyporeflexia of lower limbs are the earliest signs that appear in the children [4]. Symptoms then worsen with time. Molecular studies of PMP22 to diagnose the duplication of this gene remain the most accurate way of diagnosing CMT1A, particularly in young children in whom symptoms are not detectable yet, and also because a significant part of cases are due to a de novo mutation.

As mentioned above, CMT1A is a progressive peripheral neuropathy; by the time peripheral nerve impairment is manifested in adulthood, it may be already irreversible, or poorly reversible. Therapeutic treatment started at this stage of the disease, even if found efficient, cannot modify the early pathological events in the disease development. Accordingly, there is an unmet need for a treatment that would prevent or delay the onset of the disease.

SUMMARY OF THE INVENTION

In some embodiments, the present invention provides a new therapeutic method for treating and/or preventing CMT disease. More particularly, the invention relates to methods of treating and/or preventing CMT1A disease using PXT3003, a combination of baclofen, naltrexone and sorbitol, for example a combination of (R/S) baclofen, naltrexone, and sorbitol.

The invention in part relates to the unexpected discovery that an early treatment with PXT3003 in subjects bearing a duplication or mutation of PMP22 prevents the onset of the symptoms of the disease. It has been surprisingly found that the early administration of PXT3003 in CMT1A young subjects provides long term prevention of the manifestations of CMT1A after said treatment has been discontinued (i.e., long after the treatment). Details of the provided method are described herein infra.

DETAILED DESCRIPTION OF THE INVENTION

Figure 1:
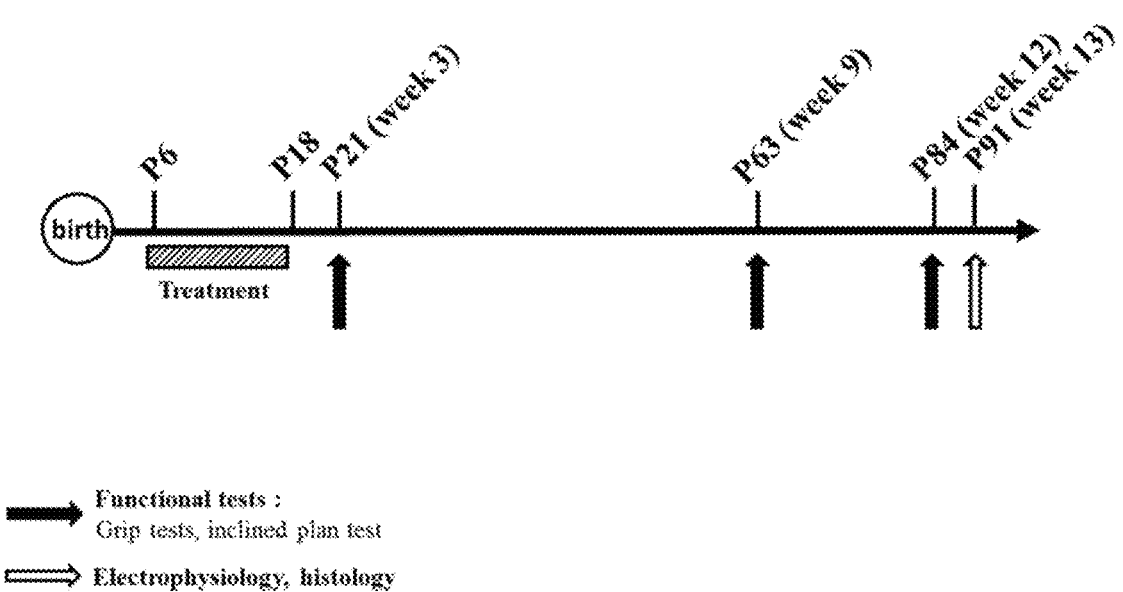
FIG. 1: Experimental design. Rats were treated with combinations of baclofen, sorbitol and naltrexone (PXT3003) or with vehicle from postnatal day 6 (P6) to day 18 (P18). Motor performances and strength of the animals were assessed at the age of 3, 9 and 12 weeks with grip strength test and inclined test. Electrophysiological measurements were carried out at an age of 13 weeks and then tissues samples were collected for histological studies.

The present invention provides new methods for treating Charcot-Marie-Tooth disease (CMT). In some embodiments, the CMT is CMT1A. The methods of the invention allow an effective treatment, prevention, or retardation of the onset of CMT1A in a subject diagnosed as overexpressing PMP22 gene, e.g. bearing PMP22 gene duplication or point mutation within PMP22 gene.

In some embodiments, the present invention provides a method of treating, preventing or delaying the onset of CMT1A in a subject in need thereof, said method comprising the steps of i) selecting a subject diagnosed or suspected to bear a duplication of PMP22 gene or a mutation of PMP22 gene, said subject being at an early stage of the disease and ii) administering to said subject a combination of baclofen (such as (R/S) baclofen), sorbitol and naltrexone, or a pharmaceutically acceptable salt thereof. In some embodiments, the present invention provides a method for treating, preventing, or delaying the onset of CMT1A in a subject bearing a duplication or mutation of PMP22 gene comprising the step of administering to said subject a combination of baclofen (such as (R/S) baclofen), sorbitol and naltrexone, or a pharmaceutically acceptable salt thereof. In some embodiments, the present invention provides a method of treating CMT1A, as described herein. In some embodiments, the present invention provides a method of preventing CMT1A, as described herein. In some embodiments, the present invention provides a method for delaying the onset of CMT1A, as described herein.

In some embodiments, the present invention provides a method for treating CMT1A in a pediatric subject in need thereof, said method comprising administering to said subject a combination of baclofen (such as (R/S) baclofen), sorbitol, and naltrexone, or pharmaceutically acceptable salt thereof. In some embodiments, the provided method comprises administering to the pediatric subject a combination of baclofen (such as (R/S) baclofen), sorbitol, and naltrexone, or pharmaceutically acceptable salt thereof, wherein the administration is transient (i.e., short term). In other embodiments, the administration is chronic (i.e., long term).

As illustrated in the Examples section, provided methods result in the long term prevention or delaying of onset of CMT1A. In a particular aspect of the invention, the combination of baclofen (such as (R/S) baclofen), sorbitol, and naltrexone is administered transiently to the subject, i.e. for a limited frame of time, while providing long term prevention or delay of the onset of the disease. Thus, the present invention is especially suited for the treatment of CMT1A in children (0-16 years old; i.e., a pediatric subject).

Definitions

Within the context of this invention, the terms "subject diagnosed or suspected to bear a duplication or mutation of PMP22 gene" and "subject bearing a duplication or mutation of PMP22 gene" refer to subject having a familial history of CMT, such as more particularly CMT1A, and/or who bears sign(s), symptom(s) or clinical evaluation(s) which are characteristic of the disease and well known to those skilled in the art. "Subject bearing a duplication or mutation of PMP22 gene" refers also to subjects presenting a spontaneous, i.e. not familial, duplication or mutation of PMP22 gene. In certain embodiments, a subject is a human.

As used herein, the phrase "bearing a duplication or mutation of PMP22 gene" refers to a subject bearing a duplication or mutation of a fragment of chromosome 17p.11 that includes the PMP22 gene and/or having at least one extra copy of the PMP22 gene.

Within the context of this invention, the terms "subject diagnosed or suspected to bear a mutation of PMP22 gene" and "subject bearing a mutation of PMP22 gene" refer to a subject diagnosed or suspected to have or having at least one of the following mutation: (i) a modification selected from c.47T>C, c.65C>T, c.68C>T, c.82C>T, 110A>T, c.117G>C, c.193G>T, c.199G>C, c.212T>C, c.215C>T, c.236C>G, c.256C>T, c.277G>C, c.314T>G, c.320G>T, c.327C>A, c.235T>A, c.353C>T, c.44T>G, c.469C>T combined with deletion of the HNPP gene; (ii) a deletion selected from c.73-78delGTCAGC, c.281delG, c.281dupG, c.312delT, c.318delT, c.344_355delCCATCTACACGG, c.434delT; (iii) splice site mutation selected from c.179-2A>G, c.319+1G>A; or (iv) a mutation resulting in a modification of the PMP22 amino acids selected from p.L16P, p.S22F, p.D37V, p.V65I, p.S72L, p.S79C, p.G93R, p.L105R, p.G107V, p.T118M, p.L147R.

In certain embodiments, the subject is a human. In some embodiments, the subject is a child of 0-16 years of age (i.e., a pediatric subject).

Current clinical scales for evaluating the stage of the CMT through impairment and disability levels of patients are CMTNS (Charcot-Marie-Tooth Neuropathy Score), CMTPedS (Charcot Marie Tooth disease Pediatric Scale) and ONLS (Overall Neuropathy Limitations Scale). CMTNS was proposed and validated by Shy et al. (2005) to provide a single and reliable measure of CMT severity [5]. CMTNS has been modified in a second version (CMTNS2) in order to provide improved sensitivity for detecting change over time and the potential effect of a treatment [6]. Hereinafter, "CMTNS" designates either of the first or the second version of CMTNS unless one particular version is specified. It is currently the sole CMT-specific outcome measure. CMTNS is a 0-36-point scale based on 9 items comprising 5 of impairment (sensory symptoms, pin sensibility, vibration, strength of arms and legs), 2 of activity limitations (motor symptoms in arms and legs) and 2 of electrophysiology (amplitudes of ulnar compound muscle action potential (CMAP) and of sensory nerve action potential (SNAP)). A CMTNS of 0 indicates the absence of sign of the disease. Higher scores indicate worsening function, and score ranges categorize disability as mild (0-10), moderate (11-20) and severe (21-36). The Charcot Marie Tooth disease Pediatric Scale score (CMTPedS) has also been used to measure disability in children with CMT from the age of 3 years [7]. CMTPedS is a 0-44-point scale based on 11 items. CMTPedS has been shown to worsen consistently throughout childhood. ONLS was derived and improved from the ODSS by Graham and Hughes (2006) to measure limitations in the everyday activities of the upper limbs (rated on 5 points) and the lower limbs (rated on 7 points)[8]. The total score ranges from 0 (=no disability) to 12 (=maximum disability). ONLS measures the perceived ability of the patient to move and fulfill normal life, and thus is expected to be associated with quality of life. Alternatively, due to the slow evolution of the disease, or at a stage of the disease where the patients are almost asymptomatic, only specific items of CMTNS as electrophysiology items can be taken into account. Consequently, in a particular embodiment, "subjects suspected to bear a duplication or mutation of PMP22 gene" relates to subjects having a familial history of CMT, more particularly CMT1A, and exhibiting results for CMTNS and/or ONLS score, or for some of their items, particularly electrophysiology assays, which are indicative of the disease.

In young subjects (aged from 3 to 10 years), including those otherwise reported as still asymptomatic, difficulties in heel walking has been found as the earliest as well as one of the most common and consistent sign of CMT1A, the other being the hypo-or areflexia in the lower limbs. Hence, in a particular embodiment, "subject suspected to bear a duplication or mutation of PMP22 gene" relates to subjects having a familial history of CMT, more particularly CMT1A, and showing difficulties in heel walking and/or hypo- or areflexia in the lower limbs.

At the earlier stages of the disease, i.e. when no or few signs or symptoms are detectable, the only way to ascertain the presence of CMT1A is to perform genetic tests to detect the duplication of PMP22 or point mutations of PMP22 which can also be a cause of CMT1A. Such genetic tests are well known from those skilled in the art and are commercially available. For example the duplication of PMP22 is usually detected using multiplex ligation-dependent probe amplification (available from e.g. MRC Holland) and completed by the analysis of specific microsatellites sequences. Thus, in a particular embodiment "subject diagnosed to bear a duplication of PMP22 gene" or "subject bearing a duplication of PMP22 gene" designates a subject for which a duplication of the PMP22 gene has been demonstrated by gene testing, this duplication being inherited, because of familial history for CMT, or arising spontaneously. Likewise, in another particular embodiment "subject diagnosed to bear a mutation of PMP22 gene" or "subject bearing a duplication of PMP22 gene" designates a subject for which at least one of the following mutation: (i) a modification selected from 47T>C, 65C>T, 68C>T, 82C>T, 110A>T, 193G>T, 199G>C, 212T>C, 215C>T, 236C>G, 256C>T, 277G>C, 314T>G, 320G>T, 327C>A, 353C>T, 44T>G, 469c>T combined with deletion of the HNPP gene; (ii) a deletion selection from 73-78delGTCAGC, 281delG, 312delT, 318delT, 343-354delGCCATCTACACG; or (iii) a splice site mutation selected from 179-2A>G, 319+1G>A has been demonstrated by gene testing, this mutation being inherited, because of familial history for CMT, or arising spontaneously. In some embodiments, the pediatric subject (i.e., patient) has not been genetically diagnosed as bearing a duplication or mutation of PMP22 gene.

Within the context of the invention the term "subject being at an early stage of the disease" includes a subject diagnosed or suspected to suffer from CMT1A for which no CMTNS or ONLS can be determined or one having a CMTNS between 0-10. In other words, the term "subject being at an early stage of the disease" includes a subject diagnosed or suspected to suffer from CMT1A as defined above for whom the disease is not detectable yet. The term "subject being at an early stage of the disease" also includes children not older than 16 years of age. In some embodiments, a subject is not older than 10 years of age, 6 years of age, 4 years of age, 2 years of age, 1 year of age, 9 months of age, 6 months of age, or 4 months of age.

As used herein, "long term prevention" or "long term reduction" refers to the continuing delay of the onset of CMT (such as CMT1A) or prevention or reduction, respectively, of a sign, symptom, or clinical manifestation of CMT, such as CMT1A, after cessation of treatment with a combination of baclofen, sorbitol, and naltrexone, or pharmaceutically acceptable salt thereof. "Long term" may refer to the entire lifetime of the subject who has undergone treatment, or may refer to a particular period of time, such as 1 month, 3 months, 6 months, 9 months, 1 year, 1.5 years, 2 years, 3 years, 4 years, 5 years, 7 years, 10 years, 15 years, 20 years, 25 years, 30 years, or longer than 30 years. "Reduction" may include a noticeable long term clinical benefit where additional chronic or intermittent treatment with the combination of baclofen, sorbitol, and naltrexone, or pharmaceutically acceptable salt thereof, and/or with other CMT treatments, is advantageous.

In some embodiments, the present invention provides a method of treating, preventing or delaying the onset of Charcot Marie Tooth type 1A disease (CMT1A) in a subject diagnosed or suspected to bear a duplication or mutation of PMP22 gene comprising the steps of:
  i. selecting a subject diagnosed or suspected to bear a duplication or mutation of PMP22 gene, said subject being at an early stage of the disease;
  ii. administering to said subject a combination of baclofen (such as (R/S) baclofen), naltrexone, and sorbitol, or a pharmaceutically acceptable salt thereof.

In some embodiments, the present invention provides a method of treating, preventing, or delaying the onset of Charcot Marie Tooth type 1A disease (CMT1A) in a subject bearing a duplication or mutation of PMP22 gene, wherein said subject is at an early stage of the disease, comprising the step of administering to said subject a combination of baclofen (such as (R/S) baclofen), naltrexone, and sorbitol, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject. In some embodiments, selecting a subject diagnosed or suspected to bear a duplication or mutation of PMP22 gene comprises detecting in said subject at least a physiological or morphological abnormality related to CMT1A disease. In some embodiments, selecting a subject diagnosed or suspected to bear a duplication or mutation of PMP22 gene comprises identifying a duplication or mutation of PMP22 gene, for example wherein the identification is made by a genetic test.

As exemplified in the experimental section, the administration of PXT3003 at an early stage of the disease results in an unexpected delay in the onset of the symptoms in an in vivo model. Moreover, such an early treatment improves physiological measures when compared to a later treatment, where the disease has progressed further. It has been surprisingly found that the administration of a combination of baclofen (such as (R/S) baclofen), sorbitol, and naltrexone at an early stage of the disease thus provides advantageous and unexpected improvements when compared to its administration when the disease is at a more advanced stage.

The Subject to be Treated

In an embodiment, the subject is at an early stage of the disease and exhibits a CMTNS comprised between 0 and 10, which corresponds to mild disability. In some embodiments, the CMTNS in said subject is not more than 8 or not more than 5. In some embodiments, the subject exhibits a CMTNS of 0, 1, 2, 3, 4, 5, 6, 7, 8, 9, or 10. In some embodiments, the subject exhibits a CMTNS of 0-8, or 0-7, or 0-6, or 0-5, or 0-4, or 0-3, or 0-2, or 0-1.

In some embodiments, the present invention provides a method of treating, preventing or delaying the onset of Charcot Marie Tooth type 1A disease (CMT1A) in a subject bearing a duplication or mutation of PMP22 gene, wherein the subject exhibits a CMTNS of 0-8, or 0-7, or 0-6, or 0-5, or 0-4, or 0-3, or 0-2, or 0-1, said method comprising the step of administering to said subject a combination of baclofen (such as (R/S) baclofen), naltrexone, and sorbitol, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject.

In an embodiment, the subject being at an early stage of the disease has an ONLS score of 0, i.e. the subject does not perceive any impairment in his overall quality of life. In another embodiment, the subject is too young to be submitted to the ONLS questionnaire.

In some embodiments, the present invention provides a method of treating, preventing or delaying the onset of Charcot Marie Tooth type 1A disease (CMT1A) in a subject bearing a duplication or mutation of PMP22 gene, wherein the subject exhibits a CMTNS of 0-8, or 0-7, or 0-6, or 0-5, or 0-4, or 0-3, or 0-4, or 0-2, or 0-1, said method comprising the step of administering to said subject a combination of baclofen (such as (R/S) baclofen), naltrexone, and sorbitol, or a pharmaceutically acceptable salt thereof, and wherein the subject is a child not older than 16 years of age, or not older than 10 years of age, 6 years of age, 4 years of age, 2 years of age, or 1 year of age. In some embodiments, the subject is a child not older than 10 years of age. In some embodiments, the subject is a child not older than 6 years of age. In some embodiments, the child is not older than 6 months of age. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject.

In some embodiments, the present invention provides a method of treating, preventing or delaying the onset of Charcot Marie Tooth type 1A disease (CMT1A) in a subject bearing a duplication or mutation of PMP22 gene, wherein the subject exhibits a CMTNS of 0-8, or 0-7, or 0-6, or 0-5, or 0-4, or 0-3, or 0-4, or 0-2, or 0-1, said method comprising the step of administering to said subject a combination of baclofen (such as (R/S) baclofen), naltrexone, and sorbitol, or a pharmaceutically acceptable salt thereof, and wherein the subject is a child not older than 16 years of age, or not older than 10 years of age, 6 years of age, 4 years of age, 2 years of age, or 1 year of age. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject.

In another particular embodiment, the subject in the method of the invention shows no other symptom than difficulties in heel walking, said subject being old enough to walk.

In another particular embodiment, the subject in the method of the invention shows no other symptom than hypo- or areflexia in the lower limbs.

In another embodiment, the subject in the method of the invention does not show any symptoms other than electrophysiological impairments. In a more particular embodiment, only amplitudes of ulnar CMAP and/or SNAP and/or radial SNAP are found altered in said subject.

In an embodiment, the subject being at an early stage of the disease exhibits a CMTPedS comprised between 0 and 30, or 0-25, or 0-20, or 0-15, or 0-10, or 0-5. In some embodiments, the CMTPedS in said subject is not more than about 20. In some embodiments, the subject exhibits a CMTPedS of 0, 1, 2, 3, 4, 5, 6, 7, 8, 9, 10, 11, 12, 13, 14 or 15. In some embodiments, the subject exhibits a CMTPedS of 0-5, or 0-10, or 0-15, or 0-20.

In some embodiments, the present invention provides a method of treating, preventing or delaying the onset of Charcot Marie Tooth type 1A disease (CMT1A) in a subject bearing a duplication or mutation of PMP22 gene, wherein the subject exhibits a CMTPedS of 0-30, or 0-25, or 0-20, or 0-15, or 0-10, or 0-5, said method comprising the step of administering to said subject a combination of baclofen (such as (R/S) baclofen), naltrexone, and sorbitol, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject.

In some embodiments, the present invention provides a method of treating, preventing or delaying the onset of Charcot Marie Tooth type 1A disease (CMT1A) in a subject bearing a duplication or mutation of PMP22 gene, wherein the subject exhibits a CMTPedS of 0-15, said method comprising the step of administering to said subject a combination of baclofen (such as (R/S) baclofen), naltrexone, and sorbitol, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject.

In a particular embodiment, the subject in the method of the invention does not show any symptoms of the disease, even though the subject bears a duplication or mutation of the PMP22 gene.

The Combination of Baclofen, Naltrexone, and Sorbitol

In some embodiments the baclofen (such as (R/S) baclofen), sorbitol, and naltrexone, or a pharmaceutically acceptable salt thereof are, in methods of the invention, administered separately to the subject. In some embodiments, the baclofen (such as (R/S) baclofen), sorbitol, and naltrexone, or a pharmaceutically acceptable salt thereof are administered simultaneously. In other embodiments, the baclofen (such as (R/S) baclofen), sorbitol, and naltrexone, or a pharmaceutically acceptable salt thereof are administered sequentially.

However, in some embodiments a single composition is used, for example for practicality and compliance reasons. Consequently, in a particular embodiment baclofen (such as (R/S) baclofen), sorbitol, and naltrexone, or a pharmaceutically acceptable salt thereof are administered in the form of a single composition. In some embodiments, the baclofen (such as (R/S) baclofen), sorbitol and naltrexone, or a pharmaceutically acceptable salt thereof are administered in the form of a single composition wherein the composition is as described in International Patent Application publication number WO 2014195394, the entirety of which is incorporated herein by reference.

The components of the combination may be administered at different doses or relative weight ratios, which may be adjusted by the skilled person, for example as a function of the age and/or weight of the subject and/or body surface area of the subject.

In some embodiments, baclofen and naltrexone are administered in provided methods of the invention at a relative weight ratio baclofen/naltrexone of between about 2:1 and about 20:1. In some embodiments, the baclofen and naltrexone are administered at a relative weight ratio of baclofen/naltrexone of between about 5:1 and about 10:1. In some embodiments, the baclofen and naltrexone are administered at a relative weight ratio baclofen/naltrexone of about 8.6:1. One of ordinary skill in the art will appreciate that the baclofen and naltrexone can be administered in a specified relative weight ratio, either separately (i.e., while maintaining the specified relative weight ratio) or together in a single composition.

In another embodiment, sorbitol and naltrexone are administered either separately or together in a single composition at a relative weight ratio sorbitol/naltrexone of between about 100:1 and about 500:1. In some embodiments, sorbitol and naltrexone are administered either separately or together in a single composition at a relative weight ratio of sorbitol/naltrexone of between about 200:1 and about 400:1. In some embodiments, sorbitol and naltrexone are administered either separately or together in a single composition at a relative weight ratio of sorbitol/naltrexone of about 300:1.

In some embodiments, baclofen, sorbitol and naltrexone are administered in provided methods of the invention at a relative weight ratio of baclofen/sorbitol/naltrexone of x/y/1, wherein:

x is between about 2 and about 20, between about 5 and about 10, or about 8.6; and y is between about 100 and about 500, between about 200 and about 400, or about 300.

In some embodiments, x is about 8.6 and y is about 300, such that the baclofen, sorbitol and naltrexone are administered in provided methods of the invention at a relative weight ratio of baclofen/sorbitol/naltrexone of 8.6/300/1.

In this regard, a particular object of the invention is a method as provided above wherein baclofen, sorbitol and naltrexone are administered either together in a single composition or separately in a relative weight ratio baclofen/sorbitol/naltrexone of x/y/1, wherein x is between about 2 and about 20, between about 5 and about 10, or about 8.6, and y is between about 100 and about 500, between about 200 and about 400, or about 300.

In another embodiment, baclofen is administered at a daily dose of between about 300 µg and about 24 mg, between about 300 µg and about 12 mg, between about 600 µg and about 6 mg, or between about 600 µg and about 1.2 mg.

In some embodiments, the present invention provides a method of treating, preventing or delaying the onset of Charcot Marie Tooth type 1A disease (CMT1A) in a subject bearing a duplication or mutation of PMP22 gene, said method comprising the step of administering to said subject a combination of baclofen (such as (R/S) baclofen), sorbitol, and naltrexone, wherein the baclofen is administered at a dose of between about 0.10 mg to about 12 mg, or between about 0.15 mg to about 0.3 mg, or between about 0.15 mg to about 0.6 mg, or between about 0.15 mg to about 1.2 mg. In some embodiments, the baclofen (such as (R/S) baclofen) is administered at a dose of about 0.1 mg. In some embodiments, the baclofen (such as (R/S) baclofen) is administered at a dose of about 0.15 mg. In some embodiments, the baclofen (such as (R/S) baclofen) is administered at a dose of about 0.2 mg. In some embodiments, the baclofen (such as (R/S) baclofen) is administered at a dose of about 0.25 mg. In some embodiments, the baclofen (such as (R/S) baclofen) is administered at a dose of about 0.3 mg. In some embodiments, the baclofen (such as (R/S) baclofen) is administered at a dose of about 0.5 mg.

The term "baclofen" as used herein generally refers to and encompasses a baclofen composition comprising solely S baclofen, solely R baclofen, or any combination of both enantiomers, while "(R/S) baclofen" refers to mixtures of the enantiomers. Thus, any reference to "baclofen" herein may be replaced with "R baclofen," "S baclofen," or "(R/S) baclofen." In some embodiments, "(R/S) baclofen" refers to a composition of baclofen comprising the R and S forms of baclofen in approximately equal amounts.

In another embodiment, sorbitol is administered at a daily dose of between about 10.5 mg and about 840 mg, of between about 10.5 mg and about 420 mg, or between about 21 mg and about 210 mg, or between about 21 mg and about 42 mg.

In some embodiments, the present invention provides a method of treating, preventing or delaying the onset of Charcot Marie Tooth type 1A disease (CMT1A) in a subject bearing a duplication or mutation of PMP22 gene, said method comprising the step of administering to said subject a combination of baclofen (such as (R/S) baclofen), sorbitol, and naltrexone, wherein the sorbitol is administered at a dose of between about 10.5 mg and about 420 mg, or between about 21 mg and about 210 mg, or between about 21 mg and about 42 mg. In some embodiments, the sorbitol is administered at a dose of about 10.5 mg. In some embodiments, the sorbitol is administered at a dose of about 21 mg. In some embodiments, the sorbitol is administered at a dose of about 100 mg. In some embodiments, the sorbitol is administered at a dose of about 420 mg.

In an embodiment, naltrexone is administered at a daily dose of between about 35 μg and about 2.8 mg, of between about 35 μg and about 1.4 mg, or between about 70 μg and about 700 μg, or between about 70 μg and about 140 μg.

In some embodiments, the present invention provides a method of treating, preventing or delaying the onset of Charcot Marie Tooth type 1A disease (CMT1A) in a subject bearing a duplication or mutation of PMP22 gene, said method comprising the step of administering to said subject a combination of baclofen (such as (R/S) baclofen), naltrexone, and sorbitol, wherein the naltrexone is administered at a dose of between about 35 μg and about 1.4 mg, or between about 70 μg and about 700 μg, or between about 70 μg and about 140 μg. In some embodiments, the naltrexone is administered at a dose of about 0.035 mg. In some embodiments, the naltrexone is administered at a dose of about 0.07 mg. In some embodiments, the naltrexone is administered at a dose of about 0.14 mg. In some embodiments, the naltrexone is administered at a dose of about 0.7 mg.

In a particular embodiment, naltrexone is administered at a daily dose of between about 70 μg and about 140 μg, baclofen at a daily dose comprised between about 600 μg and about 1.2 mg and sorbitol at a daily dose comprised between about 21 mg and about 42 mg.

In another particular embodiment, naltrexone is administered at a daily dose of between about 140 μg and about 700 μg, baclofen at a daily dose comprised between about 1.2 mg and about 6 mg and sorbitol at a daily dose comprised between about 42 mg and about 210 mg.

In a further particular embodiment, naltrexone is administered at a daily dose of between about 700 μg and about 1.4 mg, baclofen at a daily dose comprised between about 6 mg and about 12 mg and sorbitol at a daily dose comprised between about 210 mg and about 420 mg.

In some embodiments, the present invention provides a method of treating, preventing or delaying the onset of Charcot Marie Tooth type 1A disease (CMT1A) in a subject bearing a duplication or mutation of PMP22 gene, said method comprising the step of administering to said subject a combination of baclofen (such as (R/S) baclofen), naltrexone, and sorbitol, wherein the baclofen is administered at a dose of between about 600 μg and about 1.2 mg, sorbitol at a dose of between about 21 mg and about 42 mg and naltrexone at a dose between about 70 μg and about 140 μg.

In other embodiments, the present invention provides a method of treating, preventing or delaying the onset of Charcot Marie Tooth type 1A disease (CMT1A) in a subject bearing a duplication or mutation of PMP22 gene, said method comprising the step of administering to said subject a combination of baclofen (such as (R/S) baclofen), naltrexone, and sorbitol, wherein the baclofen is administered at a dose of between about 1.2 mg and about 6 mg, sorbitol at a dose of between about 42 mg and about 420 mg and naltrexone at a dose between about 140 μg and about 1.4 mg.

In an even more particular embodiment, baclofen is administered at a daily dose of about 600 μg, sorbitol at a daily dose of about 21 mg and naltrexone at a daily dose of about 70 μg. In another particular embodiment, baclofen is administered at a daily dose of about 1.2 mg, sorbitol at a daily dose of about 42 mg and naltrexone at a daily dose of about 140 μg. In a further particular embodiment, baclofen is administered at a daily dose of about 6 mg, sorbitol at a daily dose of about 210 mg and naltrexone at a daily dose of about 700 μg. In an even more particular embodiment, baclofen is administered at a daily dose of about 12 mg, sorbitol at a daily dose of about 420 mg, and naltrexone at a daily dose of about 1.40 mg. In some embodiments, these dosages are of used in cases where the subject is, for example, not older than 16 years of age, not older than 10 years of age, or not older than 6 months.

In another particular embodiment, baclofen is administered at a daily dose of about 4 mg, sorbitol at a daily dose of about 142 mg, and naltrexone at a daily dose of about 473 μg. In another particular embodiment, baclofen is administered at a daily dose of about 8 mg, sorbitol at a daily dose of about 284 mg, and naltrexone at a daily dose of about 946 μg. In some embodiments, these dosages are used in cases where the subject is a child of around 20 kg.

Alternatively, as mentioned above, said doses of baclofen, sorbitol and naltrexone, or a pharmaceutically acceptable salt thereof may be adjusted by the skilled person, for example, as a function of the age and/or weight and/or body surface area of the subject.

Administering the Combination

The components of the combination to be administered in methods of the invention may be administered in divided doses, for example two or three times daily. In a particular embodiment, baclofen, sorbitol and naltrexone, or a pharmaceutically acceptable salt thereof are formulated in a single pharmaceutical composition and administered in divided doses, for example two or three times daily. In a more particular embodiment, baclofen, sorbitol and naltrexone, or a pharmaceutically acceptable salt thereof are in a single composition which is administered twice daily. In some embodiments, baclofen, sorbitol and naltrexone, or a pharmaceutically acceptable salt thereof are administered once per day, either separately (simultaneously or sequentially) or together in the same composition.

As set forth in the experimental section, the administration of baclofen, sorbitol and naltrexone, or a pharmaceutically acceptable salt thereof to subjects in whom the disease is at an early stage is particularly advantageous. Indeed, it was surprisingly found that such an early treatment provides an improvement in particular behavioral tests for which no improvement was detectable when treatment was administered in older animals in which disease was more advanced (though treatment in older animal was shown as providing significant improvement in several other tests).

As explained above, CMT is a disease that evolves slowly with age. Symptoms of CMT1A usually first appear in infancy, most frequently in the first 10 years, generally during the first two decades. Consequently, in some embodiments, the combination is administered in subjects not older than 16 years of age, not older than 10 years of age, and even not older than 6 months.

CMT is known to be very heterogeneous, with seriousness of the disease varying greatly in patients of the same age. Consequently, in some embodiments, the present invention provides a method of treating, preventing or delaying the onset of Charcot Marie Tooth type 1A disease (CMT1A) in a subject diagnosed or suspected to bear a duplication or mutation of PMP22 gene comprising the steps of:
  i. selecting a subject diagnosed or suspected to bear a duplication or mutation of PMP22 gene, said subject being a human between 6 and 16 years of age; and
  ii. administering to said subject a combination of baclofen (such as (R/S) baclofen), sorbitol, and naltrexone, or a pharmaceutically acceptable salt thereof.

In some embodiments, the present invention provides a method of treating, preventing or delaying the onset of Charcot Marie Tooth type 1A disease (CMT1A) in a subject bearing a duplication or mutation of PMP22 gene, wherein said subject is between about 6 and about 16 years of age, comprising the step of administering to said subject a combination of baclofen (such as (R/S) baclofen), sorbitol, and naltrexone, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject. In some embodiments, selecting a subject diagnosed or suspected to bear a duplication or mutation of PMP22 gene comprises detecting in said subject at least a physiological or morphological abnormality related to CMT1A disease. In some embodiments, selecting a subject diagnosed or suspected to bear a duplication or mutation of PMP22 gene comprises identifying a duplication or mutation of PMP22 gene, for example wherein the identification is made by a genetic test. Another object of this invention relates to a method of treating, preventing or delaying the onset of Charcot Marie Tooth type 1A disease (CMT1A) in a subject diagnosed or suspected to bear a duplication or mutation of PMP22 gene comprising the steps of:
  i. selecting a subject diagnosed or suspected to bear a duplication or mutation of PMP22 gene, said subject being a human not older than 10 years; and
  ii. administering to said subject a combination of baclofen (such as (R/S) baclofen), naltrexone, and sorbitol, or a pharmaceutically acceptable salt thereof.

In some embodiments, the present invention provides a method of treating, preventing or delaying the onset of Charcot Marie Tooth type 1A disease (CMT1A) in a subject bearing a duplication or mutation of PMP22 gene, wherein said subject is not older than 10 years of age, comprising the step of administering to said subject a combination of baclofen (such as (R/S) baclofen), sorbitol, and naltrexone, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject. In some embodiments, selecting a subject diagnosed or suspected to bear a duplication or mutation of PMP22 gene comprises detecting in said subject at least a physiological or morphological abnormality related to CMT1A disease. In some embodiments, selecting a subject diagnosed or suspected to bear a duplication or mutation of PMP22 gene comprises identifying a duplication or mutation of PMP22 gene, for example wherein the identification is made by a genetic test.

A more particular object of this invention relates to the above method, wherein said subject is not older than 6 months of age.

In some embodiments, when measurable, the subject should not have a CMTNS greater than 10, or not more than 8, or not more than 5. In a particular embodiment, disregarding the age of the subject, though being diagnosed as bearing a duplication or mutation of PMP22, the subject is asymptomatic. In a particular embodiment, the only behavioral symptom of said subject is difficulty in heel walking. In another embodiment, the only symptoms are abnormalities in electrophysiological parameters, particularly Compound Muscle Action Potential and Sensory Nerve Action Potential which are well known from the skilled in the art and currently used in the diagnostic of CMT. In another particular embodiment, when measurable in regard with the age of the subject, said subject should have an ONLS score of about 0. In some embodiments, the present invention provides a method of treating CMT1A in such a subject. In other embodiments, the present invention provides a method of preventing CMT1A in such a subject. In some embodiments, the present invention provides a method of delaying the onset of CMT in such a subject.

In a very particular embodiment the human subject satisfies one of the above mentioned age criteria together with one of the symptom criteria.

A more particular object of this invention relates to a method of treating, preventing or delaying the onset of Charcot Marie Tooth type 1A disease (CMT1A) in a subject diagnosed or suspected to bear a duplication or mutation of PMP22 gene comprising the steps of:
  i. selecting a subject diagnosed or suspected to bear a duplication or mutation of PMP22 gene, said subject being a human not older than 10 years and having a CMTNS not greater than 5; and
  ii. administering to said subject a combination of baclofen (such as (R/S) baclofen), sorbitol, and naltrexone, or a pharmaceutically acceptable salt thereof.

In some embodiments, the present invention provides a method of treating, preventing or delaying the onset of Charcot Marie Tooth type 1A disease (CMT1A) in a subject bearing a duplication or mutation of PMP22 gene, wherein said subject is not older than 10 years of age and has a CMTNS of not more than 5, comprising the step of administering to said subject a combination of baclofen (such as (R/S) baclofen), sorbitol, and naltrexone, or a pharmaceutically acceptable salt thereof. In some embodiments, the present invention provides a method of treating CMT1A in such a subject. In other embodiments, the present invention provides a method of preventing CMT1A in such a subject. In some embodiments, the present invention provides a method of delaying the onset of CMT1A in such a subject. In some embodiments, selecting a subject diagnosed or suspected to bear a duplication or mutation of PMP22 gene comprises detecting in said subject at least a physiological or morphological abnormality related to CMT1A disease. In some embodiments, selecting a subject diagnosed or suspected to bear a duplication or mutation of PMP22 gene comprises identifying a duplication or mutation of PMP22 gene, for example wherein the identification is made by a genetic test.

Further to the increase of efficacy of the treatment with baclofen, sorbitol, and naltrexone combination when administered early to the subjects, it has been surprisingly found that transient administration of such combination is sufficient to delay or even prevent the onset and/or the progression of the disease for a long time after said transient administration. Indeed, more than 9 weeks after having been treated (at a time when the disease is expected to be advanced in the studied rat model for CMT disease), animals bearing PMP22 duplications display functional measures almost the same than those of wild type animals, which correlates with the observed improvements of electrophysiological parameters. Such delay of disease evolution is particularly advantageous because patients have their condition stabilized while they do not take treatment anymore. Furthermore, a dosing regimen based on a daily or even several intakes per day can be felt as burdensome and consequently raises compliance issues that should be less frequent for a treatment administered on a limited time frame.

Consequently, in a particular embodiment, the administration of baclofen (such as (R/S) baclofen), sorbitol, and naltrexone in provided methods of the invention is a transient administration of baclofen (such as (R/S) baclofen), sorbitol, and naltrexone, or a pharmaceutically acceptable salt thereof. In a more particular embodiment, this transient administration takes place during myelination process that is known to last postnatally in mammalian species. More particularly, said transient administration lasts during peak myelination process.

In a particular embodiment said transient treatment is administered for about 5 years or less, the treatment being stopped afterwards. In some embodiments, said transient administration lasts for about 1 year, or about 1.5 years, or about 2 years, or about 2.5 years, or about 3 years, or about 3.5 years, or about 4 years, or about 4.5 years, or about 5 years.

In a particular embodiment, said transient administration of about 5 years or less is applied to a subject of about 10 years of age or less, of about 6 years of age or less, or about 6 months of age or less.

In another particular embodiment, said transient treatment is administered for less than one year.

In a more particular embodiment, said transient administration lasts for between 3 to 6 months, the treatment being stopped afterwards. In some embodiments, said transient administration lasts for about 1 month, or about 2 months, or about 3 months, or about 4 months, or about 5 months, or about 6 months, or about 7 months, or about 8 months, or about 9 months, or about 10 months, or about 11 months, or about 12 months.

In an particular embodiment, said transient administration of less than one year is applied to a subject of about 10 years of age or less, about 6 years of age or less, or about 6 months of age or less.

In an even more particular embodiment, said transient administration of between 3 to 6 months is applied to a subject of about 10 years of age or less, 6 years of age or less, or 6 months of age or less.

In some embodiments, transient administration further comprises the step of regularly monitoring the subject's condition in order to detect the onset or any worsening of the disease, i.e. any worsening of already existing symptoms or any emergence of as yet unnoticed symptoms. In particular, such regular monitoring is conducted at an about one year time interval from the transient treatment, and every year after. The signature of the onset or of the worsening of the disease would be left to the interpretation of those skilled in the art or of a practitioner. Consequently, in a particular embodiment, the method of the invention incorporates the further step of assessing the evolution of CMT after the transient administration of the baclofen, sorbitol, and naltrexone. In some embodiments, transient administration of the baclofen, sorbitol, and naltrexone occurs recurrently on a one-year time interval.

For example, such a worsening or emergence may correspond to an increase of the CMTNS, or a worsening of at least one of its items. Such worsening or emergence could also correspond to an increase of the CMTPedS and/or ONLS score. A meta-analysis of the data from several clinical trials on adult subjects [9] showed that under placebo the population shows a mean deterioration of 0.16 in CMTNS and of 0.06 in ONLS score over one year. CMTPedS was shown to deteriorate consistently on an increase of around 0.5-1 point per year.

The onset or worsening of the disease can correspond to a significant fall in the value of CMAP and/or SNAP components in comparison with the previously determined corresponding data in the same subject. In particular, a significant decrease in ulnar CMAP amplitude should be interpreted as a sign of the onset or of worsening of the disease.

As already mentioned, difficulties in heel walking and/or areflexia in lower limbs have been reported as the earliest signs of the disease in young children. Also, the occurrence of such symptoms, when the patient was previously diagnosed or considered as asymptomatic, should be interpreted as the onset of the disease.

Consequently in some embodiments, the methods of the invention comprise a further step iii) of measuring recurrently, on a time interval of at about one year or less, the evolution of CMTNS and/or CMTPedS and/or ONLS and/or Compound Muscle Action Potential (CMAP) in the subject after the end of the transient administration of step ii).

In another particular embodiment, upon determination of said onset or worsening, the method of the invention further comprises a step of treating the subject either chronically (i.e. during the subject's whole life) or transiently as defined above (e.g. several years or several months) with a combination of baclofen, sorbitol, and naltrexone, or a pharmaceutically acceptable salt thereof as described herein.

In some embodiments, a treatment for CMT1A is resumed if the subject shows an increase of at least 0.15 of CMTNS and/or an increase of at least 0.5 of CMTPedS and/or an increase of at least 0.05 of ONLS that is/are measured during one of the recurrent measurements, thereby signing the onset or worsening of CMT1A in said subject. In some embodiments, the treatment that is resumed comprises chronically or transiently administering to the subject a combination of baclofen (such as (R/S) baclofen), sorbitol, and naltrexone, or a pharmaceutically acceptable salt thereof.

EXAMPLES

Early Onset Treatment with a Combination of Baclofen, Sorbitol and Naltrexone in an In Vivo Model of the CMT1A Disease 1. Animal Model The CMT transgenic rat model is a hemizygous PMP22 transgenic rat bearing three additional copies of mouse PMP22 gene. This model being characterized by dysmyelination, reduced Motor Nerve Conduction Velocities (MNCV), disminished muscle strength and sensory nerve injury [10] is considered as a sufficiently good approximation of human CMT1A disease from a clinical point of view to justify its use at a preclinical stage for several experimental CMT1A therapies [3,11]. In this model, functional symptoms of the disease appear from the age of 3 weeks.

2. Animal Husbandry

Rats were housed in a climate-controlled environment (22° C., 50% air humidity) on a 12 h light/dark cycle (lights on at 7.30 am and lights off at 7.30 pm) with free access to rodent food and water. A maximum of 7 offspring together with one adult female rat were held at the same time in cage (37 cm×54 cm). At an age of 21 days the young rats were separated from the mother and were held in a maximum of 7 animals per cage. The health status of each animal was monitored by daily assessment of weight, ataxia and behavior.

3. Animal Genotyping

Genomic DNA Isolation

Genotyping of animals was performed by standardized methods based on the polymerase chain reaction (PCR). For this purpose a tail biopsy was taken from 2 days old animals. The isolation of genomic DNA from each tail biopsy was performed according to the manufacturer's instructions using the "DNeasy Kit" from Qiagen. In brief, after addition of 180 µl ALT buffer and 20 µl Proteinase K, the tail section was incubated at 55° C. overnight. At the next morning, 400 µl AL/E buffer was added to this digestion. After a short mixing, the samples were centrifuged (1 min, 3000 rpm). The resulting supernatants (maximum 900 µl) were pipetted onto the silica membrane of the DNeasy column and then centrifuged for 1 min at 6000 rpm. Afterwards, the silica membrane was washed with 500 µl AW1 buffer (5 min, 6000 rpm) and with 500 µl AW2 (5 min, 6000 rpm). Genomic DNA was eluted with 200 µl, pre-warmed, AE buffer applied for 5 min at 60° C. to the membrane column before centrifugation (2 min, 6000 rpm). Column was reloaded with further 10 µl pre-warmed AE buffer and recentrifuged. The collected genomic DNA is stored at 4° C.

Genotype Analysis

Routine genotype analysis was performed by PCR using the isolated genomic DNA from tail biopsies and specific primers (Fwd: 5'-GACAAACCCCAGACAGTTG-3' (SEQ ID NO: 1) and Rev 5'-CCAGAAAGCCAGGGAACTC-3' (SEQ ID NO: 2)) of the mouse PMP22 transgene. PCR was carried out in a 20 µL final volume in the following reaction mix:

1 µl genomic-DNA

5 µl 10× PCR-buffer (Promega)

5 µl dNTPs (each Nucleotid f.c. 200 µM)

1 µl CPMP Fwd-Primer (f.c. 300 nM)

1 µl CPMP Rev-Primer (f.c. 300 nM)

0.3 µl Taq DNA-Polymerase (f.c.1.6 U/50 µl)

6.7 µl $H_2O$

PCR was performed in a thermocycler (T-Gradient, Biometra) using following protocol. Under these conditions a 501 bp fragment is amplified from the mouse PMP22 transgene from the DNA of the rats bearing the extra copies of PMP22. It can be detected in the 2% agarose gel. All PCRs were carried out by using positive and negative controls (the sample DNA being replaced by a known positive sample or by a corresponding volume of $H_2O$).

4. Drug Administration

TABLE 1

|  | (R/S) Baclofen (µg/kg/day) | Sorbitol (mg/kg/day) | Naltrexone (µg/kg/day) |
| --- | --- | --- | --- |
| Mix 1 | 60 | 2.1 | 7 |
| Mix 2 | 30 | 1.05 | 3.5 |
| Mix 3 | 15 | 0.525 | 1.75 |
| Vehicle (vhc) | — | — | — |

Baclofen (Sigma, (RS)-baclofen, ref 5399), sorbitol (Sigma, D-sorbitol, ref S3889) and naltrexone (Sigma, naltrexone hydrochloride, ref N3136) were dissolved in a phosphate buffer which also served as placebo (vehicle). The different mix used as a treatment in this study are detailed in table 1. Phosphate buffer composition is detailed in table 2 below.

TABLE 2

| Material | Quantity |
| --- | --- |
| Potassium dihydrogen orthophosphate (Merck) | 1.361 g |
| Disodium hydrogen orthophosphate (Sigma) | 0.175 g |
| KOH (ACS)/orthophosphoric acid (Sigma) | qs pH 5.4 |
| water for injection | qs 100 ml |

Mixes were administered once daily, 7 days per week, by oral gavage in the morning from postnatal day 6 (P6) until 18 (P18). The oral gavage was performed with a flexible canula (Harvard/Instech Solomon Plastic Feeding Tubes Order # PY2 72-4453 Instech # FTP-22-25 Plastic Feeding Tubes, 22 ga×25 mm long) in a volume of 1 ml/kg.

Mixes were administrated under a volume calculated according to the individual rat body weight measured each day before drug administration.

5. Experimental Design

After genotyping, CMT rats were treated with combinations of baclofen, sorbitol and naltrexone of different concentrations (table 1) or with vehicle, from postnatal day 6 (P6) to day 18 (P18) (FIG. 1).

Motor performances and strength of the animals were assessed at the age of 3, 9 and 12 weeks with grip strength test and inclined test. Electrophysiological measurements were carried out at an age of 13 weeks and then tissues sample were collected (FIG. 1).

Grip Strength Test

Strength/motor performances were assessed in standardized grip strength tests for forelimbs and hind limbs separately [11]. Thereby, the grip strength was measured using a digital force gauge and expressed in newtons. With their forelimbs, the animals grip a horizontal T-bar (width 14 cm, diameter 3.2 mm) connected to a gauge and the investigator pulled their proximal tail from the bar with increasing force. Hind limb grip strength is measured by supporting the forelimbs and pulling the animal's tail toward the horizontal bar. In both test variants, the maximum force exerted onto the T-bar before the animals lost grip is recorded. For each animal per limb the measure was repeated 5 times and an average force was calculated.

Inclined Plane Test

A sliding apparatus [12] of 30×50 cm Plexiglas plane that could be inclined from an angle of 0° (horizontal) up to 60° was used. Each rat was placed on the 25° inclined plane in the up-headed position (head-up orientation). Two trials separated by 1 min were performed. The Plexiglas plane was cleaned after each trial. The analysis was performed on the mean score.

The performances of rats were evaluated by a 3-level score from 0 (no slide) to 3 (the rat slides to the bottom of the plane):
score 0: no slide,
score 1: a little slide (one or two paws),
score 2: a moderate slide (4 paws) but not until the end of the plane,
score 3: the rat is sliding until the very bottom of the plane.

Electrophysiological Measurements

Nerve conduction velocities (NCVs) and compound muscle action potentials (CMAPs) were measured at the sciatic nerve and at the tail. Animals were anesthetized with a mixture of ketamine (100 mg/kg) and xylazine (20 mg/kg) administered intraperitoneally. Once anesthetized, animals were immediately placed into an oil bath (37° C.) to stabilize their body temperature for the procedure.

CMAP recordings from tail muscles in response to a single supramaximal electric stimuli of 0.1 millisecond duration to the tail nerves were performed. NCVs were calculated from the latency difference between the CMAPs after successive proximal stimulations at two sites distant from 20 mm. CMAP amplitudes were also calculated peak to peak.

Histological Analysis of the Peripheral Nerve Morphology
Tissue Treatment

At the end of the study (13 weeks, P91), animals were sacrificed using CO2 and the sciatic nerves were collected.

The removed sciatic nerves were fixed at least 1 week in 4% PFA and 2.5% GA (Karlsson and Schulz buffer, table 3). Then after fixation, each single sample was dehydrated according the protocol of table 4; afterwards, the tibial nerves were embedded in Epon (tables 4 and 5).

TABLE 3

Karlsson and Shulz buffer (qs 200 ml)

| | |
|---|---|
| NaH$_2$PO$_4$•H$_2$O | 0.36 g |
| Na$_2$HPO$_4$•2H$_2$O | 3.1 g |
| NaCl | 1 g |
| distilled water | 100 ml |
| Glutaraldehyd (25%) | 20 ml |
| formaldehyd (16%) | 50 ml |
| distilled water | 30 ml |

TABLE 4

EMTP II embedding scheme

| Step. Reagent | Time | Total time | Temperature |
|---|---|---|---|
| 1. 0.1M Na$_2$HPO$_4$-buffer | 10 min | 10 min | 4° C. |
| 2. 0.1M Na$_2$HPO$_4$-buffer | 10 min | 20 min | 4° C. |
| 3. 0.1M Na$_2$HPO$_4$-buffer | 10 min | 30 min | 4° C. |
| 4. 2% OsO$_4$ | 4 h | 4:30 h | 4° C. |
| 5. 0.1M Na$_2$HPO$_4$-buffer | 10 min | 4:40 h | 4° C. |
| 6. 0.1M Na$_2$HPO$_4$-buffer | 10 min | 4:50 h | 4° C. |
| 7. 0.1M Na$_2$HPO$_4$-buffer | 10 min | 5:00 h | 4° C. |
| 8. 30% ethanol | 20 min | 5:20 h | 4° C. |
| 9. 50% ethanol | 20 min | 5:40 h | 4° C. |
| 10. 70% ethanol | 20 min | 6:00 h | 4° C. |
| 11. 90% ethanol | 20 min | 6:20 h | 4° C. |
| 12. 100% ethanol | 10 min | 6:30 h | 4° C. |
| 13. 100% ethanol | 10 min | 6:40 h | 4° C. |
| 14. 100% ethanol | 10 min | 6:50 h | 4° C. |
| 15. propylene oxide | 10 min | 7:00 h | 4° C. |
| 16. propylene oxide | 10 min | 7:10 h | RT |
| 17. propylene oxide | 10 min | 7:20 h | RT |
| 18. propylene oxide | 10 min | 7:30 h | RT |
| 19. propylene oxide/Epon 2:1 | 2 h | 9:30 h | RT |
| 20. propylene oxide/Epon 1:1 | 2 h | 11:30 h | RT |
| 21. propylene oxide/Epon 1:2 | 4 h | 15:30 h | RT |
| 22. Epon pure | 4 h | 19:30 h | RT |

RT: room temperature

TABLE 5

Preparation of EPON

| | |
|---|---|
| Glycid Ether (Serva, 21045) | 21.4 g |
| DDSA (Serva, 20755) | 114.4 g |
| MNA (Serva, 29452) | 11.3 g |
| 10 min mix | |
| DMP-30 (Serva, 36975) | 0.84 ml |
| 20 min mix | |

Then each sample was put in a plastic template, which was filled with liquid Epon. Polymerization of the Epon was performed at 60° C. for 24 h. From this embed samples 0.5 µm thick nerve sections were cut using a rotary microtome. After stretching of the sections in a water bath, they were mounted on slides and dried for at least 5 min at 60° C. Afterwards, the nerve sections were stained with Gallyas silver impregnation for histological analysis of the peripheral nerve morphology. The embedded samples are then subjected to histological analysis via light microscopy (see below).

Morphology Analysis

To analyze the morphology of the peripheral nerves, cut sections of the tibial nerves were stained using Gallyas silver impregnation of osmicated samples standard protocol (table 6):

TABLE 6

Myelin Staining: Gallyas silver impregnation protocol

| | |
|---|---|
| 1. removing of Epon of slides by etching solution according to Maxwell [13] | 5 min |
| 2. 90%, 70%, 50% methanol | each bath for 5 min |
| 3. Washing, double distilled water. | min. 5 min |
| 4. Pyridine:acetic acid anhydride 2:1 | 30 min |
| 5. Washing, double distilled water | 10 min |
| 6. Incubation solution | Microwave 60 sec 150 watt, 10 min RT |
| 7. 0.5% acetic acid | 3 times, each 5 min |
| 8. Physical staining solution | 1-5 min |
| 9. 1% acetic acid | 3 times, each 5 min |
| 10. Washing, double distilled water | 5 min |
| 11. 2% Sodium thiosulfate | 5 min |
| 12. Washing, double distilled water | 5 min |
| 13. Alcohol and Xylol | each 5 min |
| 14. Eukitt | |

TABLE 7

Incubation solution (pH 7.4 to 7.6)

| | |
|---|---|
| Ammonium nitrate | 1 g |
| Silver nitrate | 1 g |

TABLE 7-continued

Incubation solution (pH 7.4 to 7.6)

| | |
|---|---|
| NaCl | 1 g |
| Double distilled water | 1000 ml |
| Sodium hydroxyde (4%) | 3 ml |

TABLE 8

Physical staining solution: 70 ml solution B + 30 ml solution C added to 100 ml solution A

| Solution A | |
|---|---|
| Sodium carbonate water free | 50 g |
| Distilled water | 1000 ml |
| Solution B | |
| Ammonium nitrate | 2 g |
| Silver nitrate | 2 g |
| Tungstosilicic acid | 10 g |
| Distilled water | 1000 ml |
| Solution C | |
| Ammonium nitrate | 2 g |
| Silver nitrate | 2 g |
| Tungstosilicic acid | 10 g |
| Formol 37% | 7 ml |
| Distilled water | 1000 ml |

TABLE 9

Preparation of etching solution

1. Dissolve 20 g of Potassium hydroxide in 100 ml methanol
2. Add 50 ml of propylene oxide
3. Shake for at least 30 min on ice The stained sections were photographed with a standard video frame grabber (ProgRes C14, Jenoptic) installed on a Zeiss Axiophot microscope. Overlapping photographs of the entire nerves were taken and merged using PanoToolsAssembler software. The total number of the axons per tibial nerve were counted manually by the same investigator using the CellCounter plugin of ImageJ.

The g-ratio was determined by dividing the circumference of an axon (without myelin) by the circumference of the same axon including myelin sheath. At least 100 fibers per animal were analyzed. Axonal diameter was determined from the images.

Statistical Analyses

Except when otherwise stated, all the data were analyzed by testing for a significant difference between the different experimental conditions using two-tailed t-tests.

6. Results

Safety of the Early Administration of the Mix of Baclofen, Sorbitol and Naltrexone The administration of the mix of baclofen, sorbitol and naltrexone has been found to be safe even in newborn animals, as no significant effect on the body weight (not shown) of treated animals has been detected either at P21 (21 day old rats) or P84 (84 day old rats). Further, no abnormal behavior has been noticed through the daily performed assessment of the health status the animals.

Hence, the early administration of the mix is safe in young subjects.

Figure 2:
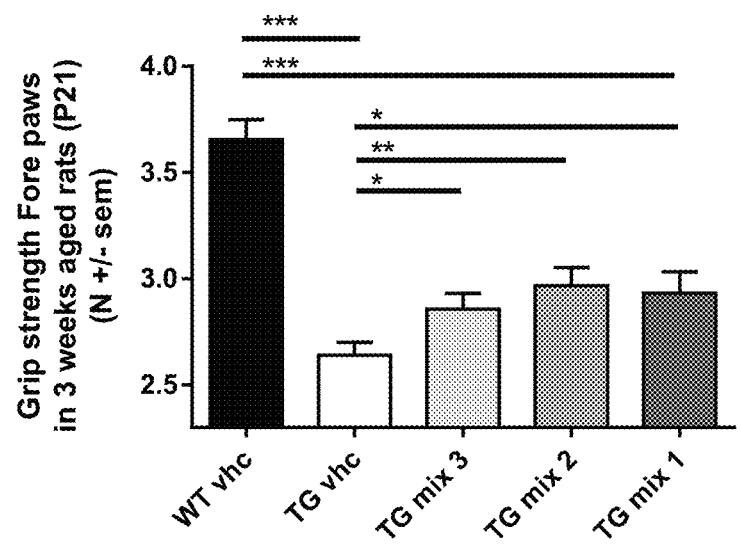
FIG. 2: Early treatment (from P6 to P18) of transgenic rats (TG) with mixes of baclofen, sorbitol and naltrexone (mixes 1-3) provides a significant improvement in grip strength (expressed in newton) of forepaws as soon as P21. Mixes 1-3 provide a significant improvement in grip strength when compared to transgenic rats administered vehicle. WT vhc: wild type animals administered with vehicle; TG vhc: TG rats administered vehicle; TG mix 1: TG rats treated with mix 1; TG mix 2: TG rats treated with mix 2; TG mix 3: TG rats treated with mix 3. *$p<0.05$; $p<0.01$; *$p<0.001$; ns: not significantly different, two tailed t-test; data are shown as mean+s.e.m.
Figure 3:
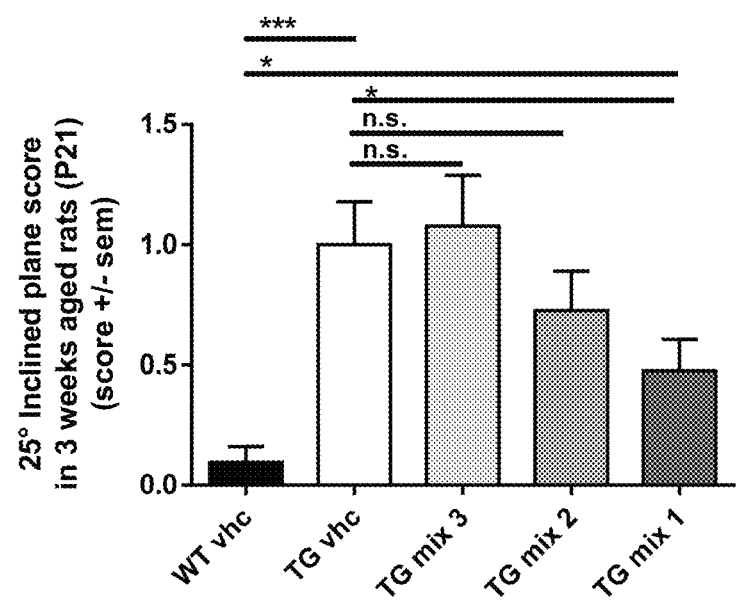
FIG. 3: Early treatment (from P6 to P18) of transgenic rats (TG) with mixes of baclofen, sorbitol and naltrexone (mixes 1-3) provides a significant improvement in motor performance (25° inclined plane test) as soon as P21. Mix 1 provides a significant improvement when compared to vehicle administered transgenic rats. A dose effect is also apparent. WT vhc: wild type animals administered vehicle; TG vhc: TG rats administered vehicle; TG mix 1: TG rats treated with mix 1; TG mix 2: TG rats treated with mix 2; TG mix 3: TG rats treated with mix 3. *$p<0.05$; ***$p<0.001$; ns: not significantly different, two tailed t-test; data are shown as mean+s.e.m.

Positive Effects of the Early and Short Term Treatment on Strength/Motor Performances are Measurable Early After the Treatment First tests were performed at P21, i.e. 4 days after the end of the 12 days early cure with the mixes. A significant improvement in grip strength tests was noticed in the treated animals as soon as 4 days after this cure. Indeed, TG treated animals perform significantly better than vehicle administered TG animals in functional measures such as grip strength or inclined plane tests (FIGS. 2 and 3). Of note, such an improvement is noticed, for the 3 mixes, even for the grip strength test (FIG. 2) for which no significant improvement had been previously evidenced in animals treated at a later stage of the disease (4 weeks, not shown) with a mix of baclofen, naltrexone, and sorbitol.

Such results clearly show the enhanced efficacy of the mix of baclofen, sorbitol, and naltrexone in treating CMT disease, when administered at an early stage of the disease (before the onset of functional symptoms.

Figure 4:
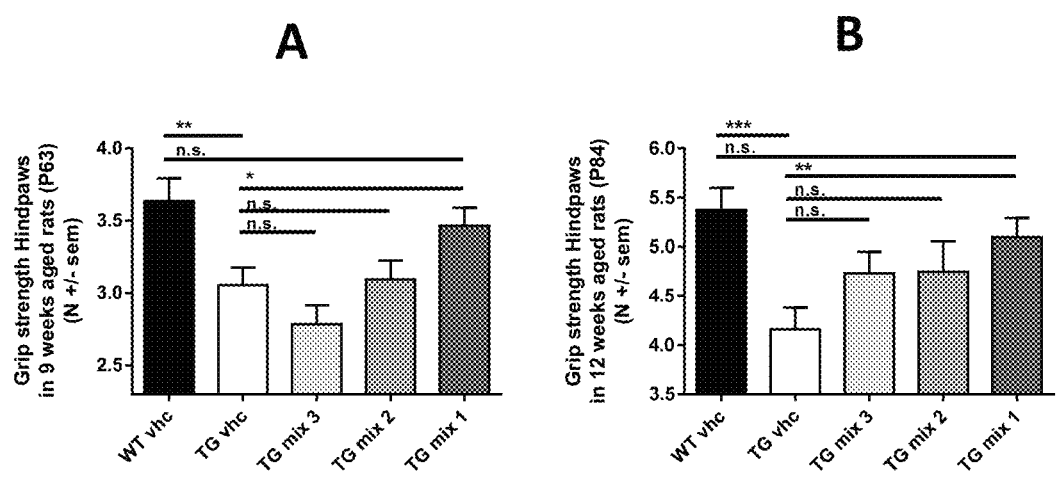
FIG. 4: Following the early and transient treatment with mixes of baclofen, sorbitol and naltrexone (mixes 1-3, from P6 to P18), improvement in grip strength (expressed in newton) of TG rats increases with time to reach performances of wild type animals. Mix 1 provides a significant improvement when compared to transgenic rats administered vehicle more than 6 weeks (A) and more than 9 weeks (B) after said transient treatment. Furthermore TG rats treated with mix 1 do not perform significantly different than vehicle administered wild type animals. A dose effect is also apparent. WT vhc: wild type animals administered vehicle; TG vhc: TG rats administered vehicle; TG mix 1: TG rats treated with mix 1; TG mix 2: TG rats treated with mix 2; TG mix 3: TG rats treated with mix 3. *p<0.05; p<0.01; *p<0.001; ns: not significantly different, two tailed t-test; data are shown as mean+s.e.m.
Figure 5:
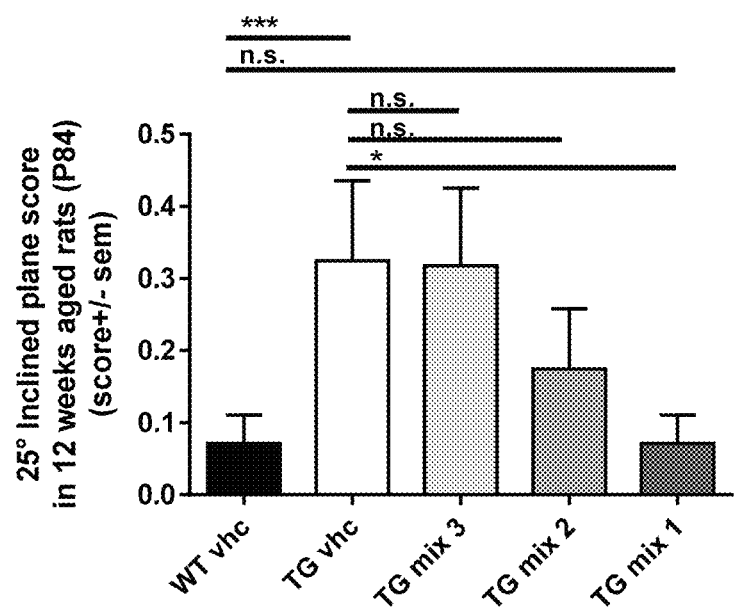
FIG. 5: Following the early and transient treatment with the mix of baclofen, sorbitol and naltrexone (mixes 1-3, from P6 to P18), improvement in motor performances (25° inclined plane test) of treated transgenic rats increases over time to equal the performance of wild type animals. Mix 1 provides a significant improvement when compared to transgenic rats administered vehicle more than 9 weeks after said transient treatment. Furthermore, TG rats treated with mix 1 do not perform significantly different than wild type animals. A dose effect is also apparent. WT vhc: wild type animals administered vehicle; TG vhc: TG rats administered vehicle; TG mix 1: TG rats treated with mix 1; TG mix 2: TG rats treated with mix 2; TG mix 3: TG rats treated with mix 3. *p<0.05, ***p<0.001; ns: not significantly different, two tailed t-test; data are shown as mean+s.e.m.

The Effect on Strength/Motor Performances Lasts and Improves Over Time, in the Absence of Treatment Measures in functional tests as well as in electrophysiological tests were also performed in rats aged of 9 weeks (P63) and 12 weeks (P84), i.e. after more than 6 and 9 weeks off treatment periods respectively. The effect of the mix 1 is found to increase with time, as performances of treated PMP22 animals are not found significantly different from those of wild type animals both in grip strength or inclined plane tests in animals of 12 weeks of age (FIGS. 4 and 5). This clearly demonstrates that the early treatment with baclofen, sorbitol and naltrexone mix allows to prevent the functional manifestations of CMT1A. Moreover, the improvement is observed in a dose dependent fashion in the two tests (FIGS. 4 and 5). The maintenance of the effect in grip test confirms the advantageous effect of early treatment with PXT3003 over a later chronic treatment.

Electrophysiological Measurements

Figure 6:
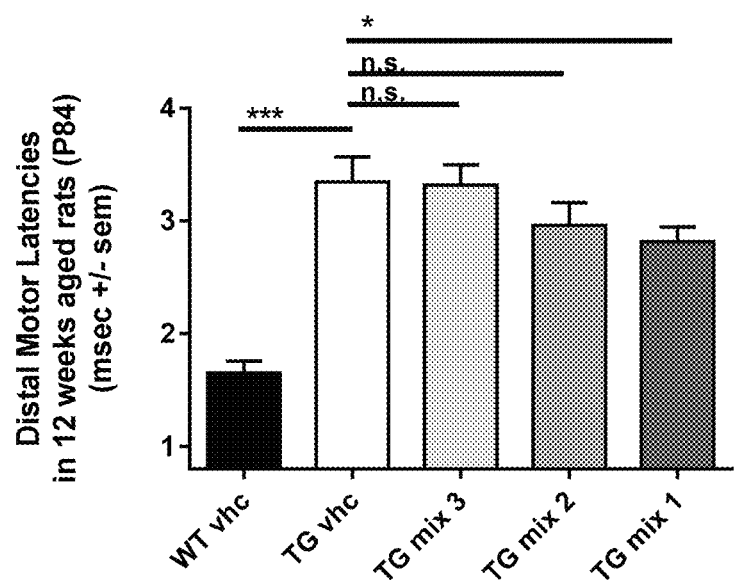
FIG. 6: Improvement afforded by the early and short term treatment with mixes of baclofen, sorbitol and naltrexone (mixes 1-3) is also detected at the electrophysiological level, more than 10 weeks after said treatment. Mix 1 treated transgenic animals also show an improvement in distal motor latency which is significantly reduced when compared to non-treated transgenic animals (TG vhc). WT vhc: wild type animals administered vehicle; TG vhc: TG rats administered vehicle; TG mix 1: TG rats treated with mix 1; TG mix 2: TG rats treated with mix 2; TG mix 3: TG rats treated with mix 3. *p<0.05, ***p<0.001, ns: not significantly different, two tailed t-test; data are shown as mean+s.e.m.

Distal motor latencies of sciatic nerves are found improved at P84 in transgenic animals treated with mix 1 from P6 to P18, when compared to vehicle administered TG animals. This indicates an improved neuromuscular transmission in treated transgenic animals (FIG. 6). A dose effect is also observed for electrophysiological measurements.

Nerve Morphology

Figure 7:
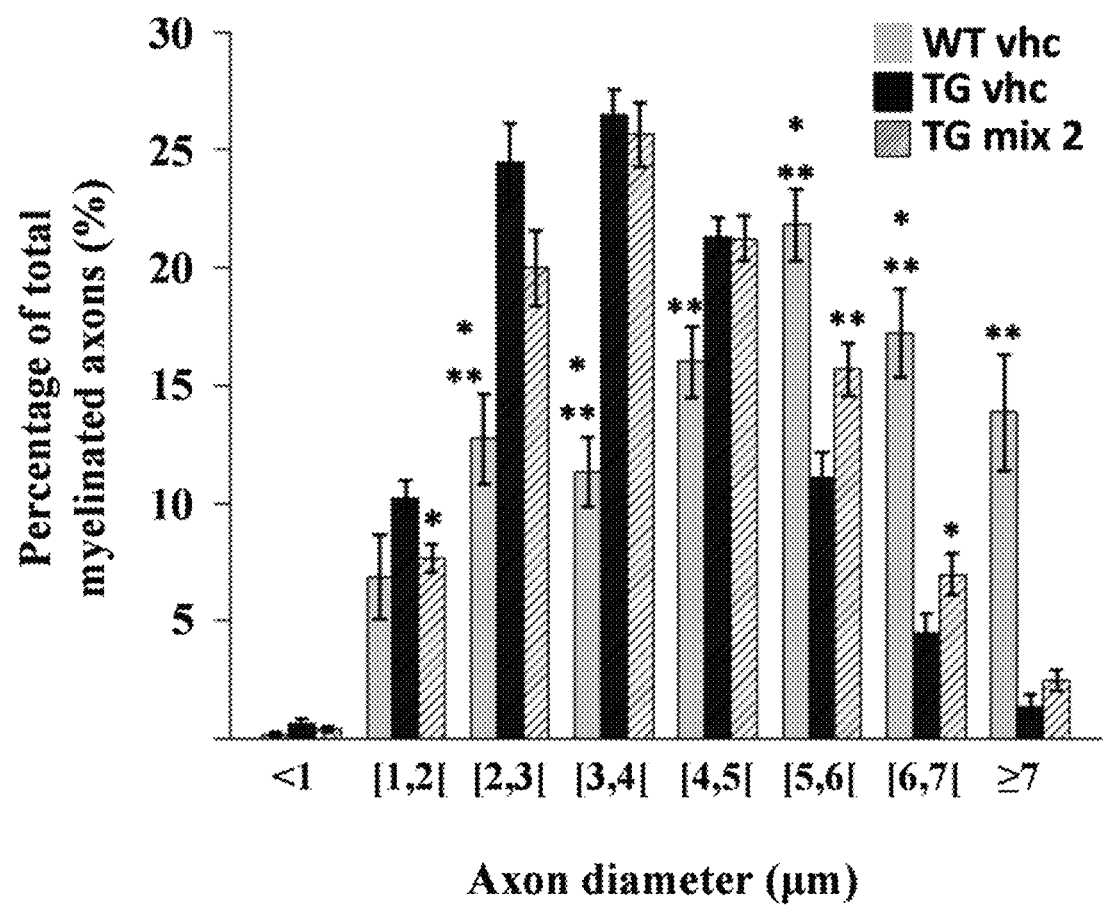
FIG. 7: Distribution of myelinated axon diameter. TG non-treated animals (black bar) are notably characterized by an increased proportion of small and medium diameter axons and by a decrease of axons of large diameter when compared to wild type animals (light grey bars). This disturbed distribution is significantly corrected in mix 2 treated TG animals (hatched bars) for axons of small and large diameter ([1 µm, 2 µm] and [5 µm, 7 µm]), when compared to non-treated TG animals. WT vhc: wild type animals administered vehicle; TG vhc: TG rats administered vehicle; TG mix 2: TG rats treated with mix 2; *p<0.05; p<0.01; *p<0.001, significantly different from non-treated TG animals, two tailed t-test; data are shown as mean+s.e.m.

It is noted that the early treatment with a mix of baclofen, sorbitol and naltrexone results in a correction of the disturbed axon caliber distribution observed in TG non treated animals. TG non treated animals are notably characterized by an increased proportion of small diameter axons and by a decrease of axons of large diameter when compared to wild type animals (FIG. 7). More than 10 weeks after the end of the early treatment, in TG PXT3003 (mix 2) treated animals, a significant increase in the number of large-caliber motor axons ([5-7] μm) as well as a significant decrease in the number of small-caliber motor axons ([1-2] μm) are observed when compared to TG vehicle administered animals (FIG. 7), which correlates with the improvement reported in strength/motor performances reported above.

Figure 8:
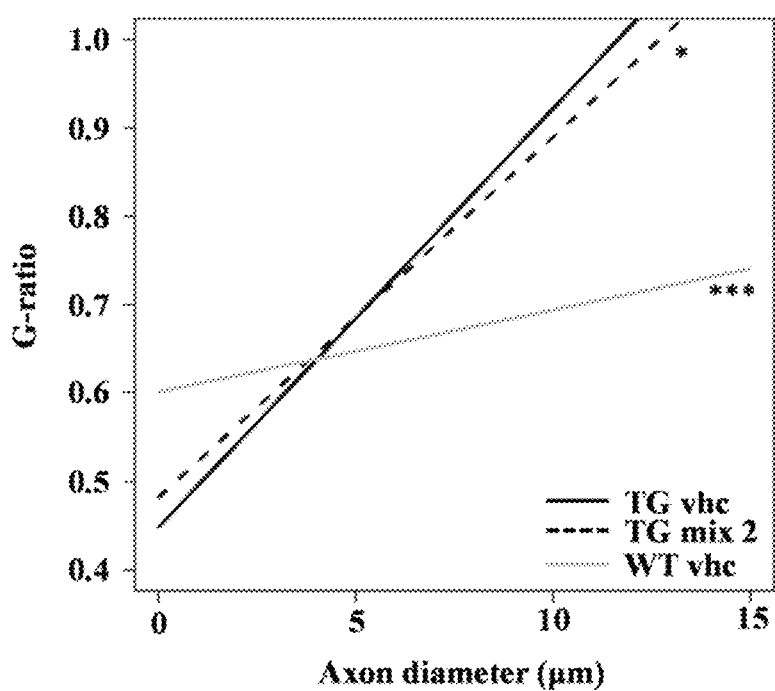
FIG. 8: Distribution of G-ratio as a function of axon diameter. In TG vehicle administered animals (black line), the distribution of G-ratio as a function of axon diameter is drastically disturbed when compared to wild type animals (light grey line). This disturbed distribution is significantly corrected in mix 2 treated TG animals (dotted), when compared to non-treated TG animals. WT vhc: wild type animals administered with vehicle; TG vhc: TG rats administered with vehicle; TG mix 2: TG rats treated with mix 2; *p<0.05; ***p<0.001, significantly different from vehicle administered TG animals, Dunnett's test.

The G-ratio, the ratio between the diameter of axon and the external diameter of the neuronal fiber, was determined (FIG. 8). The balance between the G-ratio and axon diameter is indicative of the myelination of neurons. In TG vehicle administered animals, the distribution of G-ratio as a function of axon diameter is drastically disturbed and indicates dysmyelination of the nerves. In mix 2 TG treated animals the distribution of G-ratio as a function of axon diameter is significantly normalized when compared to vehicle administered TG animals (FIG. 8), thereby showing improved nerve myelination upon treatment with PXT3003 in diseased animals.

Altogether these results demonstrate the considerable effect and advantage of early treatment over a later treatment (e.g. in young adults and older subjects) with combinations of baclofen, sorbitol, and naltrexone and substantially support the fact that such an early treatment efficiently provides long term prevention of clinical manifestation of the disease.

REFERENCES

1 Fledrich R, Stassart R M, Klink A, Rasch L M, Prukop T, Haag L, Czesnik D, Kungl T, Abdelaal T A M, Keric N, Stadelmann C, Brück W, Nave K-A & Sereda M W (2014) Soluble neuregulin-1 modulates disease pathogenesis in rodent models of Charcot-Marie-Tooth disease 1A. *Nat. Med.* 20, 1055-61.
2 Gabreëls-Festen A A, Bolhuis P A, Hoogendijk J E, Valentijn L J, Eshuis E J & Gabreëls F J (1995) Charcot-Marie-Tooth disease type 1A: morphological phenotype of the 17p duplication versus PMP22 point mutations. *Acta Neuropathol.* 90, 645-9.
3 Chumakov I, Milet A, Cholet N, Primas G, Boucard A, Pereira Y, Graudens E, Mandel J, Laffaire J, Foucquier J, Glibert F, Bertrand V, Nave K-A, Sereda M W, Vial E, Guedj M, Hajj R, Nabirotchkin S & Cohen D (2014) Polytherapy with a combination of three repurposed drugs (PXT3003) down-regulates Pmp22 over-expression and improves myelination, axonal and functional parameters in models of CMT1A neuropathy. *Orphanet J. Rare Dis.* 9, 201.
4 Haberlová J & Seeman P (2010) Utility of Charcot-Marie-Tooth Neuropathy Score in children with type 1A disease. *Pediatr. Neurol.* 43, 407-10.
5 Shy M E, Blake J, Krajewski K, Fuerst D R, Laura M, Hahn A F, Li J, Lewis R A & Reilly M (2005) Reliability and validity of the CMT neuropathy score as a measure of disability. *Neurology* 64, 1209-14.
6 Murphy S M, Herrmann D N, McDermott M P, Scherer S S, Shy M E, Reilly M M & Pareyson D (2011) Reliability of the CMT neuropathy score (second version) in Charcot-Marie-Tooth disease. *J. Peripher. Nerv. Syst.* 16, 191-8.
7 Burns J, Ouvrier R, Estilow T, Shy R, Laurá M, Pallant J F, Lek M, Muntoni F, Reilly M M, Pareyson D, Acsadi G, Shy M E & Finkel R S (2012) Validation of the Charcot-Marie-Tooth disease pediatric scale as an outcome measure of disability. *Ann. Neurol.* 71, 642-52.
8 Graham R C & Hughes R a C (2006) A modified peripheral neuropathy scale: the Overall Neuropathy Limitations Scale. *J. Neurol. Neurosurg. Psychiatry* 77, 973-976.
9 Mandel J, Bertrand V, Lehert P, Attarian S, Magy L, Micallef J, Chumakov I, Scart-Grès C, Guedj M & Cohen D (2015) A meta-analysis of randomized double-blind clinical trials in CMT1A to assess the change from baseline in CMTNS and ONLS scales after one year of treatment. *Orphanet J. Rare Dis.* 10, 74.
10 Sereda M, Griffiths I, Pühlhofer A, Stewart H, Rossner M J, Zimmerman F, Magyar J P, Schneider A, Hund E, Meinck H M, Suter U & Nave K A (1996) A transgenic rat model of Charcot-Marie-Tooth disease. *Neuron* 16, 1049-60.
11 Meyer zu Horste G, Prukop T, Liebetanz D, Mobius W, Nave K-A & Sereda M W (2007) Antiprogesterone therapy uncouples axonal loss from demyelination in a transgenic rat model of CMT1A neuropathy. *Ann. Neurol.* 61, 61-72.
12 Rivlin A S & Tator C H (1977) Objective clinical assessment of motor function after experimental spinal cord injury in the rat. *J. Neurosurg.* 47, 577-81.
13 Maxwell M H (1978) Two rapid and simple methods used for the removal of resins from 1.0 micron thick epoxy sections. *J. Microsc.* 112, 253-5.

We claim:

1. A method of treating Charcot Marie Tooth type 1A disease (CMT1A) in a subject bearing a duplication or mutation of a PMP22 gene, comprising the step of administering to the subject a combination of baclofen, sorbitol, and naltrexone, or a pharmaceutically acceptable salt thereof, effective to treat CMT1A; wherein the subject is a human of 2 years of age or less and is at an early stage of the disease.

2. The method according to claim 1, wherein the duplication or mutation of the PMP22 gene in the subject is identified by a genetic test.

3. The method according to claim 1, wherein the subject is about 1 year of age or less.

4. The method according to claim 1, wherein the subject is about 6 months of age or less.

5. The method according to claim 1, wherein the subject is showing no or few physiological or morphological signs of CMT1A.

6. The method according to claim 5, wherein the subject has a Charcot-Marie-Tooth Neuropathy Score (CMTNS) below 8.

7. The method according to claim 5, wherein the subject has a Charcot Marie Tooth Disease Pediatric Scale score (CMTPedS) below 30.

8. The method according to claim 5, wherein the subject has an Overall Neuropathy Limitations Scale score (ONLS) of 0.

9. The method according to claim 5, wherein the subject is asymptomatic.

10. The method according to claim 1, comprising administering to the subject simultaneously or sequentially a combination of baclofen, naltrexone, and sorbitol, wherein the baclofen is administered at a dose of between about 0.3 mg and about 12 mg, sorbitol at a dose of between about 10.5 mg and about 420 mg, and naltrexone at a dose between about 0.035 mg and about 1.4 mg.

11. The method according to claim 1, wherein the baclofen, sorbitol, and naltrexone are administered sequentially or simultaneously at a relative weight ratio of baclofen/sorbitol/naltrexone of x/y/1, wherein: x is between about 2 and about 20; and y is between about 100 and about 500.

12. The method according to claim 10, wherein the baclofen, sorbitol, and naltrexone are administered sequentially or simultaneously at a relative weight ratio of baclofen/sorbitol/naltrexone of about 8.6/300/1.

13. The method according to claim 12, wherein the baclofen is administered at a dose of between about 0.3 mg and about 12 mg, sorbitol at a dose of between about 10.5 mg and about 420 mg, and naltrexone at a dose between about 0.035 mg and about 1.4 mg.

14. The method according to claim 1, wherein the subject is administered a combination of (R/S) baclofen, sorbitol, and naltrexone.

15. The method according to claim 12, wherein the subject is administered a combination of (R/S) baclofen, sorbitol, and naltrexone.

16. The method according to claim 1, wherein the combination is administered chronically to the subject.

17. The method according to claim 13, wherein the combination is administered chronically to the subject.

18. The method according to claim 15, wherein the combination is administered chronically to the subject.

* * * * *